US00PP21557P3

(12) United States Plant Patent
Arias

(10) Patent No.: US PP21,557 P3
(45) Date of Patent: Dec. 7, 2010

(54) PLUM TREE NAMED 'BLACK GARABEDIAN'

(50) Latin Name: *Prunus salicina*
Varietal Denomination: Black Garabedian

(76) Inventor: Silvestre Arias, P.O. Box 7620, Fresno, CA (US) 93747

( * ) Notice: Subject to any disclaimer, the term of this patent is extended or adjusted under 35 U.S.C. 154(b) by 57 days.

(21) Appl. No.: 12/321,213

(22) Filed: Jan. 15, 2009

(65) Prior Publication Data

US 2010/0083411 P1 Apr. 1, 2010

(51) Int. Cl.
*A01H 5/00* (2006.01)

(52) U.S. Cl. ..... Plt./184

(58) Field of Classification Search ..... Plt./184
See application file for complete search history.

(56) References Cited

U.S. PATENT DOCUMENTS

PP3,133 P 4/1972 Garabedian
PP3,154 P 5/1972 Garabedian
PP5,047 P 5/1983 Garabedian
PP5,178 P 1/1984 Garabedian
PP5,291 P 10/1984 Garabedian
PP5,453 P 4/1985 Garabedian
PP5,609 P 12/1985 Garabedian
PP5,610 P 12/1985 Garabedian
PP5,902 P 3/1987 Garabedian
PP5,903 P 3/1987 Garabedian
PP5,904 P 3/1987 Garabedian
PP5,905 P 3/1987 Garabedian
PP5,906 P 3/1987 Garabedian
PP5,907 P 3/1987 Garabedian
PP5,908 P 3/1987 Garabedian
PP5,912 P 3/1987 Garabedian
PP5,987 P 5/1987 Garabedian

*Primary Examiner*—Kent L Bell
(74) *Attorney, Agent, or Firm*—Mark D. Miller

(57) ABSTRACT

A new and distinct variety of plum tree that is characterized by producing a semi freestone fruit with good dark red coloration and is ripe for commercial harvesting and shipment June 3-June 14 in the San Joaquin Valley of Central California. The new variety is closely similar to 'Santa Rosa' plum (non patented) from which it is hybridized but it is distinguishable in that it ripens seven to ten days before 'Santa Rosa' variety. The fruit of this new variety is medium size with good flavor and good dark red color which makes it greatly acceptable for the consumer.

1 Drawing Sheet

BACKGROUND OF THE NEW VARIETY

The present invention refers to a new variety of plum which will hereinafter be denominated as the 'Black Garabedian' plum tree. The 'Black Garabedian' is a medium size dark red fruit with yellow flesh that is mature for harvesting and shipping in the June 3 to June 14 period in a normal year in the San Joaquin Valley of Central California.

In the development of new commercial varieties specific characteristics provide a premium on those fruit varieties that mature early or late in the growing season. However, in particular early varieties lack size, flavor and coloration on blush. Therefore, in order for a fruit to be a success, it must be of good size, have flavor, good color, and also have good holding/storage and shipping characteristics. In addition, the date of maturing must be different from other similar fruit. This new invention meets all of the aforementioned criteria and therefore would be of commercial appeal to the consumer.

ORIGIN AND ASEXUAL REPRODUCTION OF THE NEW VARIETY

The present invention (variety) was discovered by the inventor, Silvestre Arias, on a varietal test block near the city of Fresno, Calif. The invention was discovered as a hybrid of 'Santa Rosa' (non patented) and 'El Dorado' (non patented) plum trees. The new variety was asexually reproduced in the dormant season of 2005 by bud grafting 60 acres (1200 trees)

on Nemared rootstock about seven to eight miles from the original planting. The inventor carefully compared the asexually reproduced trees with the parent hybrid including the fruit and found that they are identical in all respects.

SUMMARY OF THE NEW VARIETY

'Black Garabedian' plum tree is characterized by producing a medium semi-free stone fruit which has a very good blush coloration and is ripe for commercial eating and shipping around June 3 to June 14 in a normal year in the San Joaquin Valley of Central California as a medium fruit with dark red blush and yellow flesh. The new variety is most similar to 'Santa Rosa' plum tree (non patented) from which it is a prodigy but distinguishable in that it ripens seven to ten (7-10) days before the 'Santa Rosa' variety or the 'El Dorado' variety. The fruit of this new variety is medium size with good flavor and good dark red color which makes it greatly acceptable to the consumer.

BRIEF DESCRIPTION OF THE DRAWINGS

The accompanying colored photograph shows the following: foliage including stem and new growth at the upper right; below this foliage is a fruit cut in half displaying the pit well in the upper half and the pit in the well in the lower half; below the cut fruit is additional terminal foliage; between the two sets of foliage is a pit; to the right of the pit is a side view of a ripened fruit; and along the bottom, from left to right, is another side view, a bottom view and a top view of a ripened fruit.

DETAILED DESCRIPTION

Referring more specifically to the horticultural details of the new and distinct variety of plum trees, the following descriptions have been observed under the ecological conditions prevailing at the origin orchard near Fresno, Calif. in the San Joaquin Valley of Central California. All major color designations are by reference to the Dictionary of Color by Maerz and Paul, First Edition, published in 1930. Common colors are also employed.

TREE

Size: Medium, for the observed three year old tree.
- *Height.*—10-11 feet (304.8-335.3 cm).
- *Width.*—8-9 feet (243.8-274.3 cm).
- *Vigor.*—Three year old tree reached height of 11-12 feet.
- *Hardiness.*—Tolerance for chilling temperatures during dormancy.
- *Shape.*—Pyramid — upright.
- *Productivity.*—Very good for three year old tree.
- *Regularity of bearing.*—Regular.
- *Chilling requirements.*—Normal for plum trees in the Central San Joaquin Valley of California.

TRUNK

Size: Medium—15.0 inches (38.1 cm) circumference, 14.0 inches (35.6 cm) above ground.
Surface texture: Rough.
Color code: Vineyard Operto+(55-L-12).
Lenticels:
- *Number.*—Many.
- *Size.*—Length 0.08-0.16 inch (2.0-4.0 mm).

BRANCHES

Size: Medium — 6.0-8.0 inches (15.2-20.3 cm) in circumference at approximately 3 years.
Angle of branches: 52° from vertical.
Color:
- *One year or older.*—Wineberry (55-H-4).
- *Less than one year old.*—Fern (21-I-7).

LEAVES

Size: Medium.
- *Length.*—3.15-3.94 inches (8.0-10.0 cm).
- *Width.*—1.38-1.77 inches (3.5-4.5 cm).

Shape: Ovate.
Margin: Double serration.
Apex: Broadly acute.
Base: Broad.
Surface texture:
- *Upwardly disposed surface.*—Smooth.
- *Downwardly disposed surface.*—Slightly rough.

Glands: 2 small.
- *Color.*—Green (24-L-7).

Stipules: 1-3.
- *Color.*—Maroon (7-L-7).

Upwardly disposed leaf surface: Chrome Gr. Deep (24-H-12).
Downwardly disposed leaf surface: Art Gr. (22-L-7).
Young terminal leaves display with: Rhododendron (54-J-6).
Petiole:
- *Length.*—0.43-0.59 inch (1.1-1.5 cm).
- *Diameter.*—0.08 inch (0.2 cm).
- *Color.*—Fern (21-I-7).

Midvein:
- *Width.*—0.04 inch (1.5 mm).
- *Color.*—Rainette Gr. (21-K-4).

FLOWERS

Flower buds:
- *Shape.*—Conic.
- *Size.*—Length: 0.16-0.20 inch (4.0-5.0 mm). Width: 0.06-0.20 inch (3.0-5.0 mm).
- *Number.*—3-4 per cluster.

Calyx: 5 sepals.
- *Color.*—(19-J-8), slightly darker than Calliste Gr. (19-L-6).

Date of first bloom:
- *Feb.* 10, 2008.—10-15%.
- *Feb.* 28, 2008.—100%.
- *Flowers generally showy.*—Size: small, in clusters of 3-4. Diameter of typical flower when fully opened: Average 0.71 inch (18.0 mm). Quantity: Abundant.

Petals: 5.
- *Size.*—Small. Length: 0.31-0.39 inch (8.0-10.0 mm). Width: 0.28-0.35 inch (7.0-9.0 mm).
- *Form.*—Broadly ovate.
- *Color (upper and lower surfaces).*—White.
- *Claws.*—Small, length — 0.04 inch (1.0 mm).
- *Petal margins.*—Undulate. Shape: Truncate.
- *Pedicel.*—Average length 0.39-0.51 inch (10.0-13.0 mm).
- *Sepals.*—Number: 5. Color (entire)-(19-J-8), but darker than Calliste Gr. (19-L-6). Stamens: 16-20.
- *Filament.*—Color — white.
- *Anthers.*—Small. Color: Nugget Bronze Y (11-L-8).
- *Pistil.*—Longer than stamens. Color: Sky Gr. (18-I-5). Number: 1.
- *Fertility.*—Pollinators: 'Showtime' — 'Santa Rosa'.

FRUIT

Date of maturity: June 3-June 14.
- *Date of first picking.*—First week of June.
- *Date of last picking.*—Mid-June.

Size: Medium.
- *Weight.*—4 fruit — 1.5 pounds (42.5 grams).
- *Diameter of axial plane.*—1.97-2.05 inch (50-52 mm).
- *Transverse in suture plane.*—2.44-2.64 inch (62-67 mm).
- *Transverse at right angle to suture plane.*—2.64-2.68 inch (67-68 mm).

Form: Globose.
Stem cavity:
- *Length.*—0.71-0.79 inch (18-20 mm).
- *Width.*—0.71 inch (18 mm).
- *Depth.*—0.31 inch (8 mm).

Stem:
- *Length.*—0.47-0.51 inch (12-13 mm).
- *Width.*—0.08 inch (2 mm).
- *Apex (front).*—Rounded.
- *Pistil point.*—Unnoticeable.

*Skin.*—Thickness normal for plum.
*Texture.*—Firm.
Skin:
*Bloom amount.*—Moderate.
*Tendency to crack.*—Minimal.
*Tenacity.*—Holds well on tree.
Color:
*Blush.*—Burgundy (56-E-8).
*Ground.*—Dark Cardinal Rose lustre (6-L-8).
*Flesh.*—Near skin: Chartreuse (11-L-1). Remainder: Pyrethrum Y. (11-L-2).
*Texture.*—Firm.
*Aroma.*—Mild.
*Eating quality.*—Very good.
*Flavor.*—Very good.
*Juice.*—Very good.
*Surface of cavity.*—Burnished gold (12-L-7).
*Pit well.*—Burnished gold (12-L-7).
Pit well:
*Length.*—0.91 inch (23 mm).
*Width.*—0.71 inch (18 mm).
*Depth.*—0.31-0.35 inch (8-9 mm).
Use: Fresh market.
Keeping quality: Excellent.
Shipping quality: Very good.
Harvest date: June 3-June 14.

STONE

Semi freestone
Fibers: Few.
Size:
*Length.*—0.91 inch (23 mm).
*Width.*—0.79 inch (20 mm).
*Thickness.*—0.47 inch (12 mm).
Form: Ovate.
Apex shape: Somewhat rounded.
Color (dry): Chrome Op (10-K-12).
Base: Somewhat flattened.
Sides:
*Ventral.*—Slightly winged.
*Dorsal.*—Ridged from apex to base.
Tendency to split: None observed.

The plant showed no evidence of any disease during the growing season.

The above description of this new variety of plum tree is based on the growing conditions prevalent in the Fresno area of the San Joaquin Valley of Central California. Variations of the usual magnitude, such as maturity date and production may be due to cultural practices including irrigation practices, fertilization, fruit planning and primary climate changes.

What is claimed is:

1. A new distinct plum tree as described and illustrated that is similar to the 'Santa Rosa' plum (not patented) which is one of the parents, but is distinguished in that the fruit is somewhat larger, has more dark red skin coloration with excellent flavor and stores well, maturing seven to ten days before 'Santa Rosa'; and is also similar to 'Black Amber' (non patented) but has yellow flesh compared to 'Black Amber' and matures four to seven days before 'Black Amber'.

* * * * *

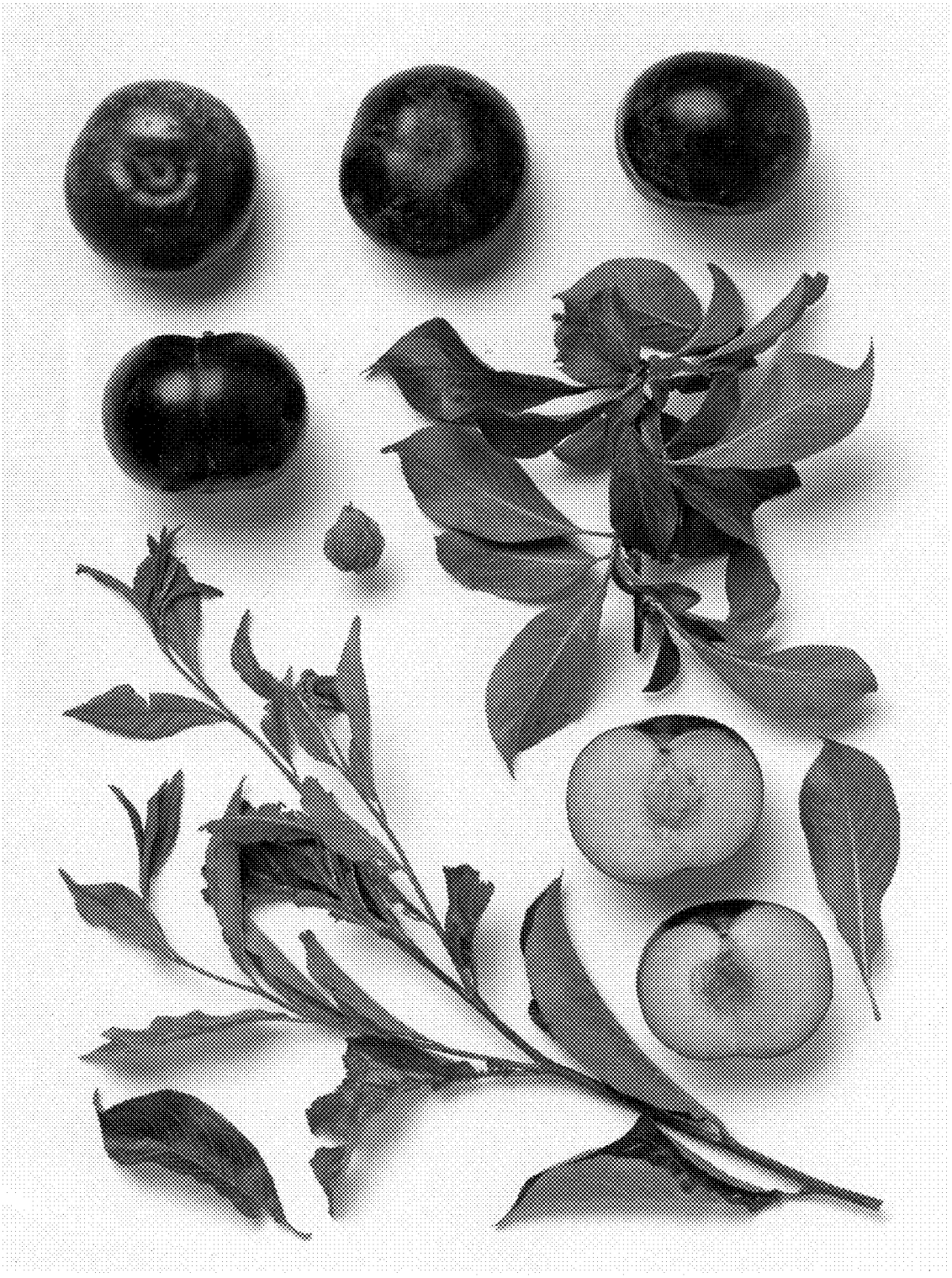

UNITED STATES PATENT AND TRADEMARK OFFICE

CERTIFICATE OF CORRECTION

PATENT NO. : PP21,557 P3
APPLICATION NO. : 12/321213
DATED : December 7, 2010
INVENTOR(S) : Silvestre Arias It is certified that error appears in the above-identified patent and that said Letters Patent is hereby corrected as shown below:

Cover page, after item (22) insert

-- Related U.S. Application Data

(63) Continuation of application No. 12/242,289 filed on September 30, 2008. --

At Column 1, Line 3, insert

-- This application claims the benefit of U.S. utility application No. 12/242,289 filed on September 30, 2008, which is incorporated herein by this reference in its entirety. --

Signed and Sealed this
Fifteenth Day of February, 2011

David J. Kappos

David J. Kappos
*Director of the United States Patent and Trademark Office*